US011157842B2

United States Patent
Pinho et al.

(10) Patent No.: US 11,157,842 B2
(45) Date of Patent: Oct. 26, 2021

(54) SYSTEM, EQUIPMENT AND METHOD FOR PERFORMING AND DOCUMENTING IN REAL-TIME A REMOTELY ASSISTED PROFESSIONAL PROCEDURE

(71) Applicants: Mauro de Souza Leite Pinho, Joinville (BR); Thiago Magalhães Bramante, Votorantim (BR); Miguel Angelo Pedroso, Itu (BR)

(72) Inventors: Mauro de Souza Leite Pinho, Joinville (BR); Thiago Magalhães Bramante, Votorantim (BR); Miguel Angelo Pedroso, Itu (BR)

(73) Assignee: ILTEC—LUBECK TECNOLOGIA LTDA, Itu (BR)

( * ) Notice: Subject to any disclaimer, the term of this patent is extended or adjusted under 35 U.S.C. 154(b) by 641 days.

(21) Appl. No.: 15/544,439

(22) PCT Filed: Jan. 28, 2016

(86) PCT No.: PCT/BR2016/050015
§ 371 (c)(1),
(2) Date: Jul. 24, 2018

(87) PCT Pub. No.: WO2016/119034
PCT Pub. Date: Aug. 4, 2016

(65) Prior Publication Data
US 2018/0336500 A1    Nov. 22, 2018

(30) Foreign Application Priority Data
Jan. 28, 2015 (BR) .......................... 102015001999-8

(51) Int. Cl.
*G06Q 10/06* (2012.01)
*H04W 4/80* (2018.01)
(Continued)

(52) U.S. Cl.
CPC ............. *G06Q 10/06* (2013.01); *G16H 10/40* (2018.01); *G16H 20/40* (2018.01); *G16H 80/00* (2018.01); *H04L 65/60* (2013.01); *H04W 4/80* (2018.02)

(58) Field of Classification Search
CPC ........ G06Q 10/06; G16H 10/40; G16H 80/00; H04W 4/80; G06F 19/3481; H04L 65/60
(Continued)

(56) References Cited

U.S. PATENT DOCUMENTS

| 9,769,332 B1* | 9/2017 | Delaunay ........... H04N 1/00244 |
| 2004/0070674 A1* | 4/2004 | Foote ....................... H04N 7/18 |
| | | 348/207.99 |

(Continued)

OTHER PUBLICATIONS

Andrius Budrionis, An Evaluation Framework for Defining the Contributions of Telestration in Surgical Telementoring, 2013 (Year: 2013).*

(Continued)

*Primary Examiner* — Tonia L Dollinger
*Assistant Examiner* — Schquita D Goodwin
(74) *Attorney, Agent, or Firm* — Laurence P. Colton; Smith Tempel Blaha LLC

(57) ABSTRACT

A real-time user connection system and equipment for device connection and signal transmission for telecommunications, real-time connection, distance assisted professional procedures and telemedicine. The system provides the performing and documenting of real-time distance assisted professional procedures, being applicable to distance assisted surgeries and distance assisted examinations. The equipment for transmitting a signal SE originating from at least one signal source has at least one encoder, which encodes the signal and sends an output signal S1, which is forwarded to a user group, and at least one user, located at (Continued)

remote base, sends information to a device located at a local base through a communication channel.

13 Claims, 6 Drawing Sheets

(51) Int. Cl.
*G16H 10/40* (2018.01)
*G16H 80/00* (2018.01)
*H04L 29/06* (2006.01)
*G16H 20/40* (2018.01)

(58) Field of Classification Search
USPC .......................................................... 709/217
See application file for complete search history.

(56) References Cited

U.S. PATENT DOCUMENTS

| | | | | |
|---|---|---|---|---|
| 2007/0248261 A1* | 10/2007 | Zhou | ....................... | G16H 30/40 382/154 |
| 2008/0212677 A1* | 9/2008 | Chen | .................... | H04N 19/194 375/240.16 |
| 2009/0097548 A1* | 4/2009 | Karczewicz | ........... | H04N 19/61 375/240.03 |
| 2010/0049824 A1* | 2/2010 | Hu | ...................... | H04N 21/6175 709/217 |
| 2012/0072024 A1* | 3/2012 | Wang | ..................... | B25J 9/1689 700/259 |
| 2012/0182244 A1* | 7/2012 | Arthur | ..................... | G06F 3/023 345/173 |
| 2013/0236158 A1* | 9/2013 | Lynch | ................ | H04N 21/4331 386/231 |
| 2013/0275561 A1* | 10/2013 | Phillips | ................... | H04L 65/80 709/219 |
| 2014/0176661 A1* | 6/2014 | Smurro | .................. | G16H 20/40 348/14.06 |
| 2015/0002541 A1* | 1/2015 | Dillavou | ..................... | G06F 3/011 345/633 |
| 2015/0025392 A1* | 1/2015 | Zhao | ....................... | G06T 11/00 600/476 |
| 2015/0070585 A1* | 3/2015 | Sharif-Ahmadi | ........................... | H04N 21/4667 348/564 |
| 2016/0210411 A1* | 7/2016 | Mentis | ................... | G16H 30/20 |

OTHER PUBLICATIONS

B and H Cerevo LiveShell, May 28, 2013, p. 1, retrieved from the Internet URL:https://www/youtube.com/watch?v=1 DX0ovz2nto.

* cited by examiner

SYSTEM, EQUIPMENT AND METHOD FOR PERFORMING AND DOCUMENTING IN REAL-TIME A REMOTELY ASSISTED PROFESSIONAL PROCEDURE

STATEMENT OF RELATED APPLICATIONS

The application is the US PCT National Phase of International Application No. PCT/BR2016/050015 having an International Filing Date of 28 Jan. 2016, which claims priority on Brazil Patent Application No. 10 2015 001999-8 having a filing date of 28 Jan. 2015.

BACKGROUND OF THE INVENTION

Technical Field

The present invention belongs to the fields of telecommunications, real-time connection, real-time distance assisted professional procedures and telemedicine. More specifically, the present invention describes a real-time user connection system and an equipment connecting devices and transmitting signals. The system of the invention enables the performing and documenting of real-time distance assisted professional procedures, being applicable to real-time distance assisted surgeries and distance assisted medical examinations.

Prior Art

Communication devices are present in the daily routine of the population, such as computers, PDAs, tablets, smartphones, etc. With this advancement, it is now possible to connect various users, who can exchange text messages, audio messages, recorded and real-time video messages, among other variations. These advancements allow users to communicate from all over the world.

Such devices are also applied in industrial scale, where they connect various types of equipment, such as industrial process machines, etc., communicating said equipment with the proper control systems, so as said actions can be performed remotely, i.e., without the need of a technician on site.

Other applications include the field of education, in which classes are provided to students in a non-classroom manner, in remote environments and which communicate with professionals/professors of the chosen field. There are also cases in which said devices are used in the medical fields, such as in the training of new professionals. In these applications, a medical expert remotely aids a physician that is operating equipment, or even performing a surgery. In these situations, the communication devices must have extreme reliability, in addition to providing the connection of more than one expert following the process remotely to further improve the aid to the physician who is performing said task locally—this increases reliability of the procedure even in places where access is difficult or where there is lack of specialized professionals in the procedure being performed.

When searching the background art in the scientific and patent literature, some documents have been found dealing with the topic, being only partially relevant in the context of the present invention:

Document US2003083563 describes a system for acquisition and transmission of data obtained through local medical equipment, wherein non-processed data are transmitted to a remote base, where it is processed by a technician/physician expert in the field and forwarded to the local equipment with the appropriate modifications. Such solution, however, implies in the fact that the equipment allocated in the remote base requires high data processing capacity for assembling the image sent. In addition, such solution does not allow other users to receive and/or modify data sent by the local base, as this is a point-to-point communication.

Also known are equipment and systems to aid professional/surgical procedures via distance professional/preceptorship support, which provide image and/or voice data transmission in an online or near-online manner. However, said equipment requires sophisticated connection and/or data transmission facilities, have complex structure and are often inaccessible to facilities in the place where the procedure is performed. In addition, said equipment does not provide online video image editing by the professional/preceptor that is remote, so as that the professional/physician that performs the procedure locally would receive the edited video information online along with the audio.

Equipment and systems currently known enable a type of communication that requires high processing capacity in the remote base, i.e., the system must be robust, implying in an increased implementation cost.

Thus, from what is evident in the researched literature, no document has been found anticipating or suggesting the teachings of the present invention, such that the solution proposed herein, to the eyes of the inventors, is novel and has inventive step over the prior art.

BRIEF SUMMARY OF THE INVENTION

The present invention aims to solve the problems of the prior art by means of the development of a system, equipment and process for performing and documenting a real-time distance assisted professional procedure. The system of the invention comprises:

a local device or equipment, where the professional/medical procedure is performed, provided with means for receiving, reproducing/playing and transmitting video and audio signals;

one or more device(s) or remote equipment(s), provided with means for receiving, reproducing/playing and/or editing and online video and audio transmission to the device;

said local and remote device(s) being connected by communication network(s), providing passive or active online monitoring by a professional/preceptor, without requiring sophisticated or complex facilities.

The inventive concept common to all contexts of protection claimed in the present invention, which provides the simplicity of the system/equipment/process, is the simultaneous presence of the following functions: an audio and video signal encoder; a router, these being associated with a network switch in which the encoder receives an input signal and sends an output signal to a virtual address, so as to provide the remote and real-time connection to a local user and at least one remote user. In the present invention, these functions are exemplified by way of an embodiment which is the equipment that is also an object of the invention.

In a first object, the present invention discloses a system for performing and documenting a real-time distance assisted professional procedure comprising:

a. an equipment (21) for transmitting a signal (S1) from an input signal (SE) emitted by at least one signal source (20), such equipment (21) comprising:

a video encoder adapted to receive an input signal (SE) and configured to send an output signal (S1);

b. a virtual address (22) receiving the signal (S1) emitted by the equipment (21), directing said signal (S1) to at least one server (23); and c. such server (23) directing the signal (S1) to at least one communication channel (C1), providing access to at least one user (24, 25).

In one embodiment, said user (24) is a spectator and does not edit the audio and video signals remotely. In another embodiment, said user (25) is a participant that accesses a communication channel (C2), emits at least one signal (S2) to at least one device (26) configured to receive said signal (S2).

In a second object, the present invention discloses an equipment for performing and documenting a real-time distance assisted professional procedure, said equipment comprising:

a. at least one encoder (12);
b. at least one router (13); and
c. at least one network switch (14);

where said encoder (12) and said router (13) are associated with the network switch (14);

said encoder (12) being adapted to receive an input signal (SE) and configured to send an output signal (S1) to a virtual address (22).

In a third object, the present invention discloses a process for performing and documenting a real-time distance assisted professional procedure, said process comprising the audio and video transmission from the local user to a remote professional, both using the equipment/system of the invention, such that the procedure performed locally by the user is assisted in real time and remotely by the remote professional.

In one embodiment of said process, the signal source (20) of an image capture device is connected to at least one image processor, said image processor sending an input signal (SE) directly to the above-described equipment (21). The equipment is associated with and is an integral part of the system, such that the communication channel (C2) comprises a command signal (S2), sent by at least one participant (25) to the device (26) that performs such command.

In one embodiment, the process of the invention is applied to industrial processes. In another embodiment, the process of the invention is applied to medical procedures.

These and other objects of the invention shall be immediately considered by persons skilled in the art and by companies having interests in the segment, and shall be described in sufficient details for its reproduction in the following description.

BRIEF DESCRIPTION OF THE DRAWINGS

With the aim of better defining and clarifying the contents of the present patent application, the following figures are presented.

DETAILED DESCRIPTION OF PREFERRED EMBODIMENTS

The descriptions that follow are presented only by way of example and are non-limiting of the scope of the invention and will enable a clearer comprehension of the objects of the present patent application.

The inventive concept common to all contexts of protection claimed in the present invention, which provides the simplicity of the system/equipment/process, is the simultaneous presence of the following functions: an audio and video signal encoder, a router, these being associated with a network switch, in which the encoder receives an input signal and sends an output signal to a virtual address, so as to provide the distance and real-time connection to a local user and at least one remote user. In the present invention, these functions are exemplified by way of an embodiment which is the equipment that is also an object of the invention. To date, there is no available equipment that integrates all functions of the system of the invention, such that, in the present description, part of the system functions are performed by the equipment of the invention. The persons skilled in the art shall immediately understand that part or all of the functions of the system of the invention may be integrated in equipment or applications without leaving the spirit and the scope of the present invention.

In another embodiment, the process of the invention is applied to medical procedures.

For the training of a professional in the surgical field, significant care is needed, since the unprepared professional may end up putting patient lives at risk. Even with due preparation, with the completion of courses, etc., the professional may feel insecure at the moment of a surgery, requiring an instruction from a better prepared specialist.

Thus, the present invention relates to equipment associated with a system that allows the connection of users arranged at a local base with users arranged at a remote base, such that the communication presents reliability, where the user at the remote base sends relevant information to aid the ones arranged at the local base.

Figure 1:
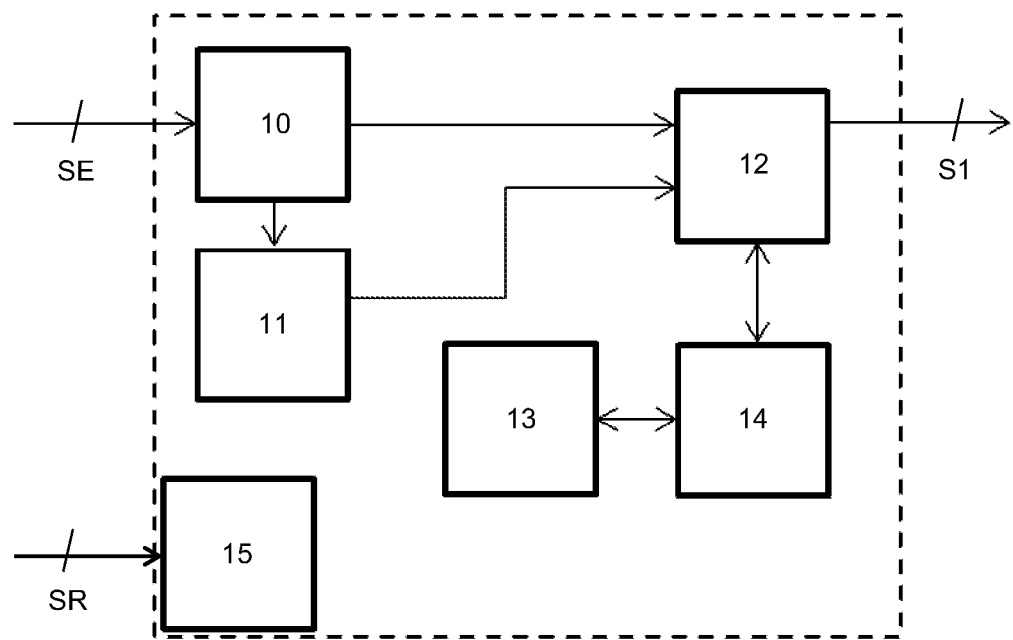
FIG. 1 shows the block diagram of interconnections of an embodiment of the system presented in the present invention.

In FIG. 1, the interconnection scheme of said equipment described in the present invention is shown. The switching device (10) is connected to a signal converter (11) and to an encoder (12), where an input signal (SE) is directed by the switching device (10) to said signal converter (11) or to said encoder (12), so as to rely on the application. In one embodiment, the input signal (SE) is a digital video signal, and the signal converter (11) is of the digital to analog converter type.

Said equipment additionally comprises a router (13) and a network switch (14) to perform the connection to an external network. To accomplish this, the encoder (12) and router (13) are associated with the network switch (14).

Encoder (12) is configured so as to receive the input signal (SE), either from the switching device (10) or from the signal converter (11), and send an output signal (S1), appropriate to the type of information carried, to a virtual address (22). In an embodiment, said encoder (12) is an analog video encoder, such as, for example, 480p, so as to receive analog video and send video in the proper standard to said virtual address (22).

To avoid connection problems during the operation of said equipment, encoder (12) is configured so as to adjust the output signal (S1) as a function of quality of the network connection detected. In one embodiment, said encoder (12) uses the RTMP (Real Time Messaging Protocol) protocol to send data as the output signal (S1). Such setting allows the equipment to be arranged in places having Internet connection problems, which have a small band for real-time video transmission, such as hospitals installed in areas far away from urban centers.

In one embodiment, the router (13) provides Wi-Fi and wired connection when using the local base network, and 3G/4G-type connection. Such router (13) being configured so as to preferably use the local base network and, in the moment of a connection loss, is switched to the 3G/4G network in a manual or automated way.

Additionally, said equipment of the present invention comprises a sound signal emission device (15), said sound signals being forwarded by a received signal (SR) of a communication device.

Figure 2:
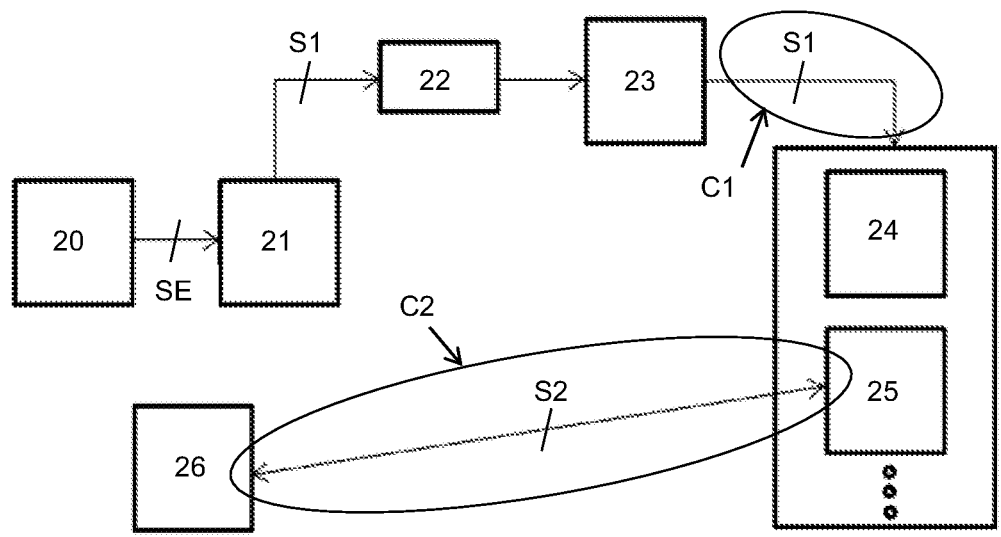
FIG. 2 shows the block diagram of interconnections of an embodiment of the equipment (21) presented in the present invention.
Figure 3:
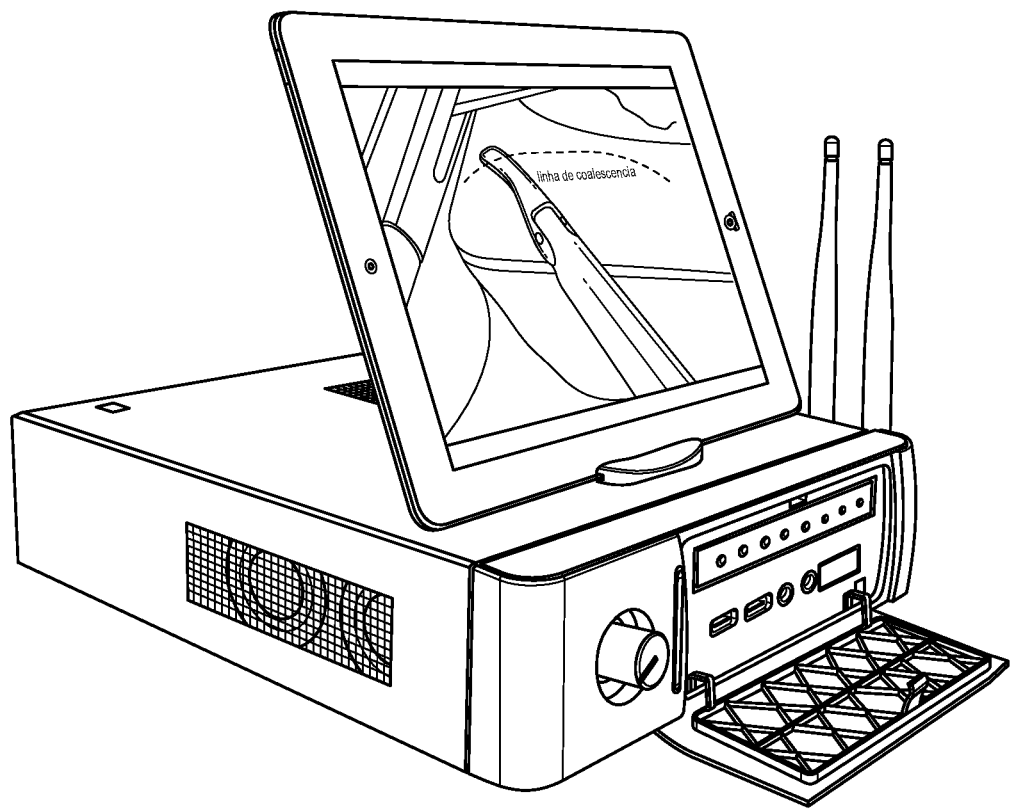
FIG. 3 shows a perspective view of an embodiment of the equipment presented in the present invention.
Figure 4:
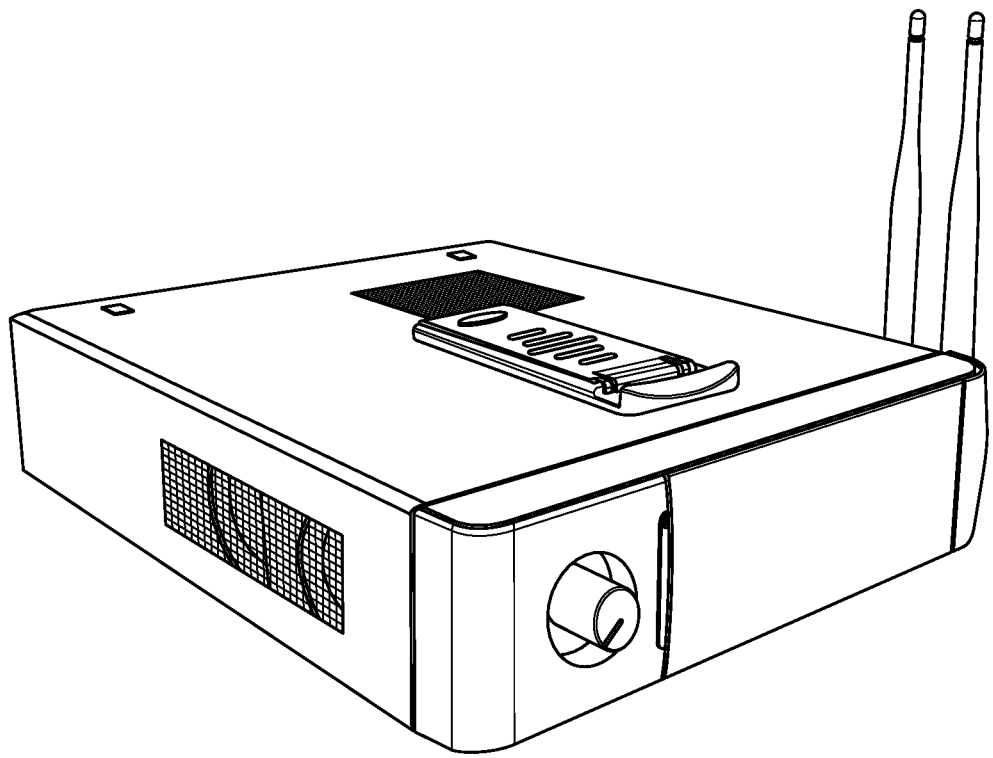
FIG. 4 shows a second perspective view of an embodiment of the equipment presented in the present invention.
Figure 5:
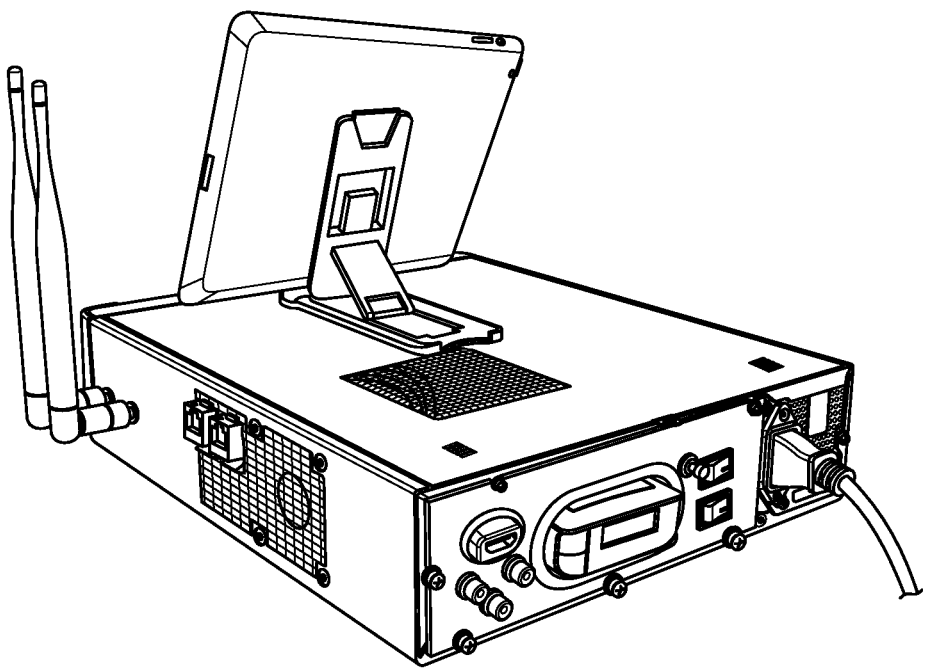
FIG. 5 shows a back view of an embodiment of the equipment presented in the present invention.
Figure 6:
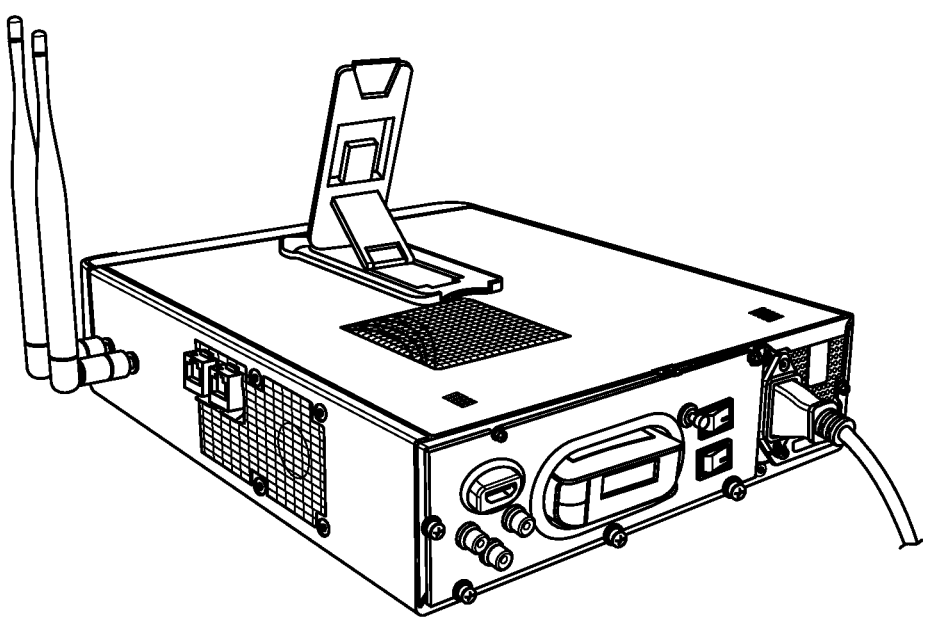
FIG. 6 shows a second back view of an embodiment of the equipment presented in the present invention.
Figure 7:
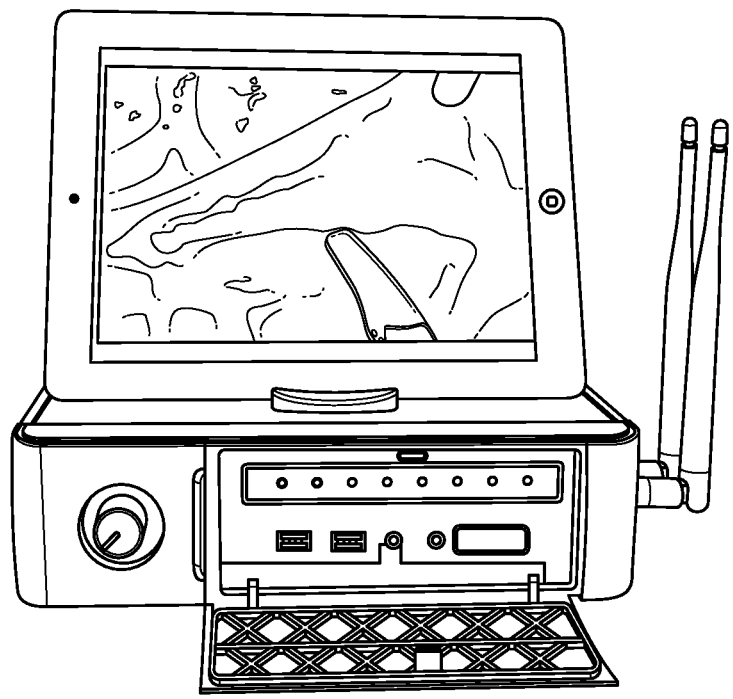
FIG. 7 shows a front view of an embodiment of the equipment presented in the present invention.
Figure 8:
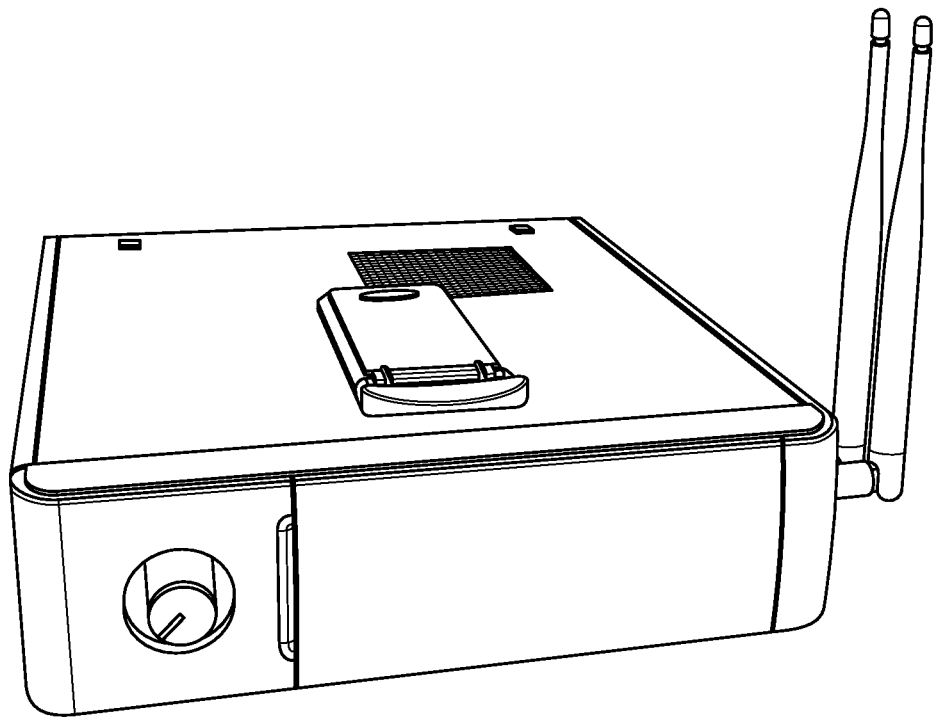
FIG. 8 shows a second front view of an embodiment of the equipment presented in the present invention.

The system of the invention provides connection of users in real time, as presented in FIG. 2. The system consists of a signal source (20) sending an input signal (SE) to equipment (21) which, in turn, sends an output signal (S1). Wherein the equipment (21) comprises a video encoder configured for such function, where, further, the same is adapted to adjust the output signal (S1) quality as a function of the Internet connection quality detected at the communication channel (C1).

For the system operation, the equipment (21) used is any device able to provide data communication with the Internet and allow graphical visualization of an input signal (SE) and transmission of an output signal (S1), such as, for example, a computer, laptop, tablet, etc. Further, by video encoder it is meant a means to adapt the input signal (SE) to an appropriate network transmission protocol, in this case, the RTMP standard. In one example, for such function, the equipment (21) used is the equipment previously defined, comprising the encoder (12) for adjusting the input signal (SE). In a second example, the equipment (21) is a laptop adapted with a video capture card, for example, a Dazzle Video Creator, which provides the reception of the input signal (SE). Further, the laptop is adequate so as to convert the input signal (SE) to the output signal (S1) in the standard protocol adequate to the system operation, such as, for example, RTMP.

With this, the signal (S1) is, thus, forwarded to a virtual address (22), connected to the Internet network, which has the goal of directing the signal (S1) to a server (23). Said virtual address (22), in one embodiment, is an access link redirected to specific pages, in this case, to the server (23).

Said server (23) directs the signal (S1) to a communication channel (C1), wherein a group of several users, arranged at a remote base, is connected and receives said signal (S1). The group is restricted to a controlled number of users that access the information contained in the signal (S1) through a usual security system, so that only enabled users may have access to the information. In an embodiment, the security is given by means of an access key of the "user and password" type.

In the system presented in the present invention, the user described may be a spectator (24) or a participant (25). The spectator (24) only receives the information and analyzes the data obtained. In the case of a participant (25), the same, from another communication channel (C2), is able to send information through a signal (S2) to a device (26), arranged at a local base, configured to receive said signal (S2). In one example, this fact provides that a physician arranged at a local base and performing a surgery involving video signals is aided by a specialist, at a remote base, who analyzes the video sent by the physician and sends information relevant to the surgery performed.

In an embodiment, the communication channel (C2) is of the videoconferencing type, wherein the participant (25) communicates with the device (26) through video calls. In another embodiment, the communication channel (C2) is of the screen sharing type, where the participant (25) performs commands on the screen used and the signal (S2) is send to the device (26) screen. The communication channel (C2), in another example, is based on the combination of videoconferencing and screen sharing.

The communication channel (C2) allows that other participants (25) and spectators (24), contained in the group of users, have access and participate in the information contained in the signal (S2) carried out by the participants (25) and sent to the device (26). Thus, in one example, when a specialist, taken as a participant (25), aids a professional located at a local base, other specialists participate in the connection, who are able to give opinions and debate on the orientation transmitted.

In an embodiment, the participant (25) receives the signal (S1), such signal (S1) being a video signal, from the communication channel (C1), and, thus, performs graphics editions in the received video by means of a software configured for such function, sending the signal (S2) via the communication channel (C2) configured to operate via screen-sharing. Such signal (S2) is received by the device (26), which the user arranged at the local base has access to. In addition, signal (S2), having a graphical modification of signal (S1), is also shared among other users comprised in the user group.

Device (26), in the present invention, relates to electronic equipment, such as a computer, tablet, smartphone. With this, in order to connect said device (26) to the Internet network, router (13) is used, arranged at said equipment (21), wherein router (13) provides a wired or wireless connection using Wi-Fi or 3G/4G technology.

The fact that the communication channel (C2) is preferably of the bidirectional type, it allows the device (26) to send data to the user group consisting of spectators (24) and participants (25). Thus, when device (26) is operated by a user, the same can send information from the local base, such as a voice signal, video and text messages.

The system presented in the present invention allows a user, which is arranged at a local base, to communicate with a user arranged at remote bases, with no user limitation and in a closed group. In given locations, Internet access is extremely restricted, thereby, the system and equipment proposed allow data transmission such that the rate is adjustable to the local connection, in addition to comprise more than one means for connecting, impacting an increased product reliability in case of extreme care, such as in a surgery or in a medical examination.

The examples shown herein are intended to only exemplify one of many ways of carrying out the invention, without, however, limiting the scope thereof.

Example 1—Process for Performing Remotely Assisted Surgery

One example of implementation of the system comprising the equipment (21) presented in the present invention is the assisted surgery application, where a physician in a local base is performing a surgery involving the use of video signals, and the same is assisted by a specialist in a remote base.

An image capture device is used in the surgery, for example, inserted inside a patient, and sends captured images to equipment configured to receive the video signal, performing image processing. Such image processing equipment is taken as said signal source (20) referred to in the present invention, so that the processed video is the input signal (SE) sent to the equipment (21), where such equipment is the equipment for transmitting the signal received by a signal source, object of the present invention, comprising the encoder (12).

In the example, the input signal (SE) is a digital video signal, thus, the same is directed by the switching device (10), to the signal converter (11) for converting the digital video signal to analog video signal, so as to make it compatible with what is supported by the encoder (12). The signal, then, is forwarded to said encoder (12) to perform the encoding of said output signal (S1). The quality of the Internet connection is then verified by the encoder (12) so that the same can adjust the output signal (S1) quality. Thereby, the signal, then, is encoded and sent to a previously configured virtual address (22).

Said virtual address (22) is based on an address director, such as an Internet link, so as to direct the signal (S1) to a server (23) configured for such function. Signal (S1) is forwarded to the communication channel (C1), where said signal (S1) is made available for a group having several users. The users are specialist physicians that assist the physicians performing the surgery, being divided into spectators (24) and participants (25), which have access to video after going through the security process, where a user name and configured password are entered.

The user group, then, receives the video sent by the physician performing the surgery. A specialist physician taken as a participant (25), through the communication channel (C2), assists the physician performing the surgery. The communication channel (C2) is configured to operate in screen sharing mode, where the image comprised on the participant (25) equipment screen, such as, for example, a computer or a tablet, is sent via signal (S2) to the device (26) where the physician performing the surgery is located.

By means of a graphics editing software, participant (25) modifies the image received from signal (S1), so as to highlight, for example, the location in which the surgeon physician must perform an incision. With the device (26), such as a tablet, computer, or a pair of smart glasses, the doctor receives the image from signal (S2) with the indications that the specialist made and, thus, puts them into practice.

Device (26) is configured to connect to the Internet network via a Wi-Fi connection provided by the router (13) arranged in the equipment (21).

The communication channel (C2) also allows voice communication among users, so that, in addition to the edited images, the specialist physician talks to the physician performing the surgery. Equipment (21) comprises active loudspeakers (15) that receive the audio signal through signal (SR) originating from the device (26).

Example 2—Signal Transmission Equipment

As can be seen in FIGS. 3-8, the equipment proposed in the present invention is applied to information signal transmission, formed by an association of elements, where it consists of an encoder (12) able to receive audio and/or video signals, being analog and/or digital video, converting the signal to an RTMP proper network standard protocol. Encoder (12) used in the system embodied in the present invention is preferably encoder (12) model Cerevo LiveShell, where it receives a video signal of up to 480i NTSC or 576i PAL. Said encoder model (12) has been chosen due to the fact that it has resources for adjusting image quality according to the Internet connection available for transmission, in addition to showing the flexibility of composite video and digital video inputs, which appropriate for low bit rate broadcasting standards.

To provide the adjustment of the signal transmitted according to the Internet connection, encoder (12) was configured so as to transmit at a rate of 2000 kbps, where the Internet connection was given via fiber optics, where transmission rates are adjusted according to the connection speed. The rates available are predefined in 2000 kbps, 800 kbps, 500 kbps and 300 kbps, where an operator may perform such adjustment manually according to the quality of the image received.

In the equipment, a network switch (14) is included, wherein model TP-Link® with five 10/100 Mbps ports was used, with flow control in IEEE 802.3x, supporting a high information traffic rate and able to provide data communication between encoder (12) and router (13).

Further, router (13) is preferably of the model TP-Link® portable Wireless N 3G/4G TL-MR3020, which was chosen due to the ability to perform Internet signal routing from a 3G/4G modem. Said router (13) model allows operation in three modes: WAN mode, wherein router (13) receives an Internet signal via network cable and routes said signal to the other Wi-Fi receivers; AP mode, wherein router (13) receives the Internet signal via Wi-Fi provided with an external network generated in the equipment implementation environment, such as, for example, a local Wi-Fi network, and through this, generates an autonomous network, i.e., regardless of the local network in the environment, able to provide Internet connection to the receiving elements; 3G/4G mode, wherein router (13) receives the signal from a 3G/4G modem connected to a USB port, and routes the Internet signal to the network receivers in question.

To turn on the equipment, an electrical supply means is provided, which consists of an external source able to provide electrical supply to all elements that make up the equipment. Each element of the equipment comprises an independent power supply, i.e., encoder (12) requires an individual power supply, which the router (13) and switch (14) also require. Thereby, the equipment supply means consists of the individual element supplies concentrated in a single cabinet, which is arranged externally to the equipment itself. Further, the equipment supply means is able to provide supply to a device (26) used in the real-time user connection system.

Such arrangement of the electrical supply means allows the equipment to have decreased weight, decreased internal space and, mainly, decreased electromagnetic field generated by the operation of said element supplies, which electromagnetically interfere with the transmission signals.

The equipment further comprises a video converter (11) able to perform HDMI video to composite video conversion, in one example, 1080p video input with analog video output having 480i NTSC or 576i PAL resolution.

In addition, said equipment comprises a sound signal emitting device (15) being loudspeakers of the model Multilaser SP089 with 4 W RMS power, 150 Hz-14000 kHz (3 dB) frequency response, USB connection or 5V/1000 mA and SNR>85 dB.

Example 3—Assisted Surgery

Figure 9:
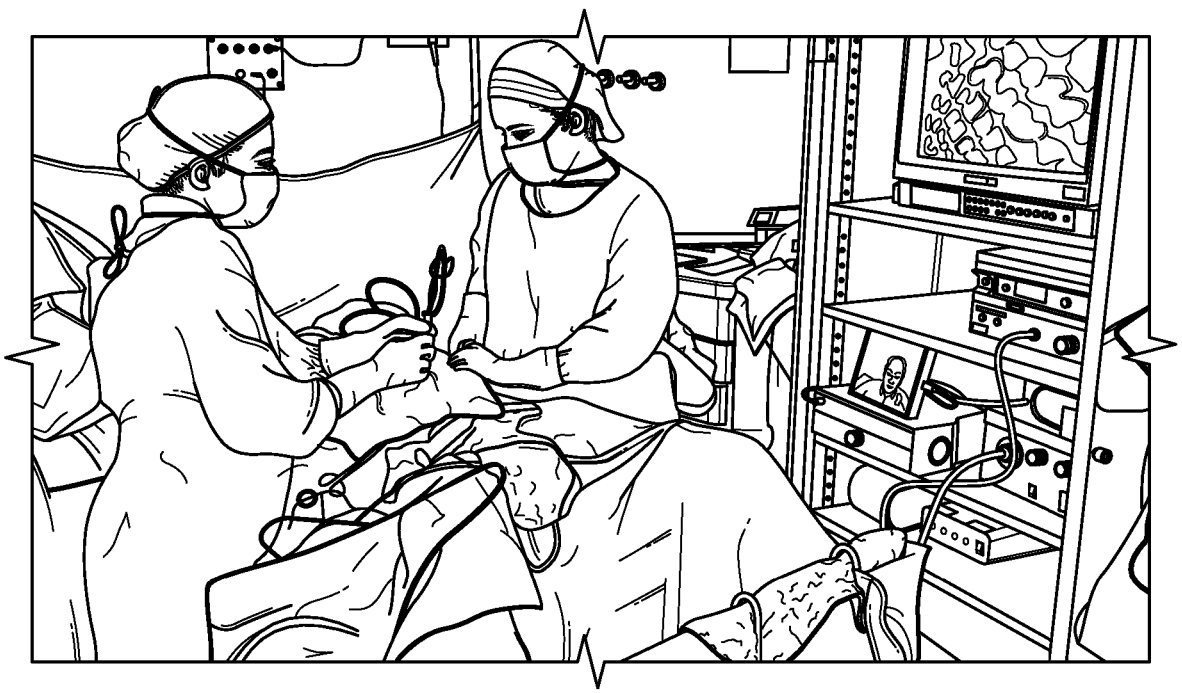
FIG. 9 depicts a real procedure with the use of the system proposed in the present invention.
Figure 10:
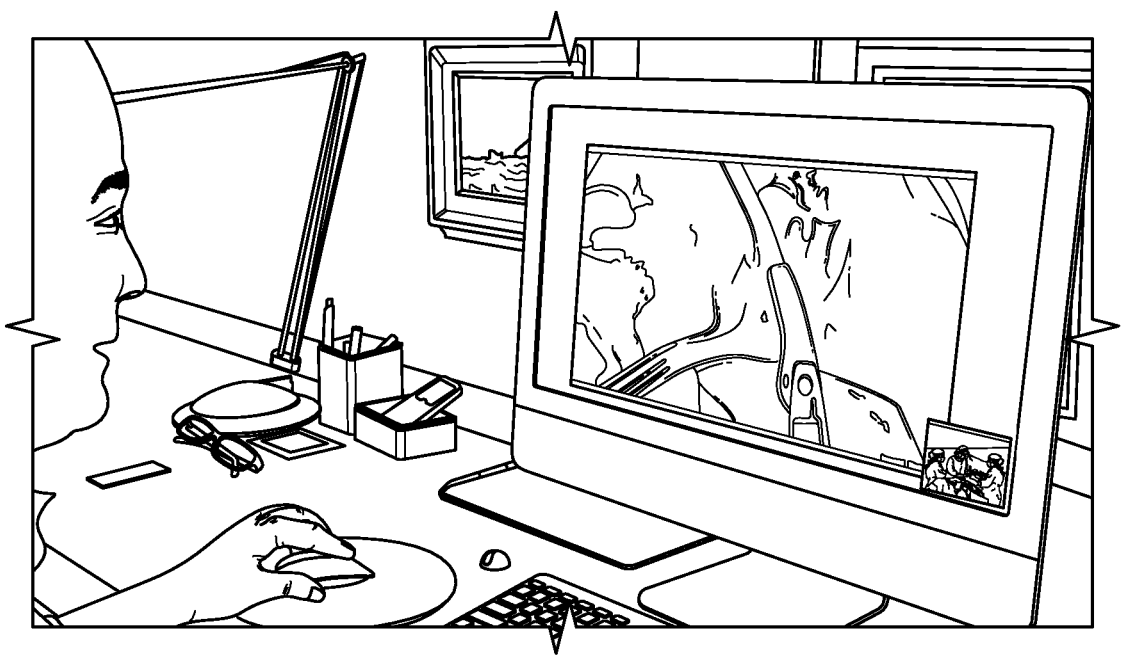
FIG. 10 depicts the image visualization by a preceptor using the system proposed in the present invention.
Figure 11:
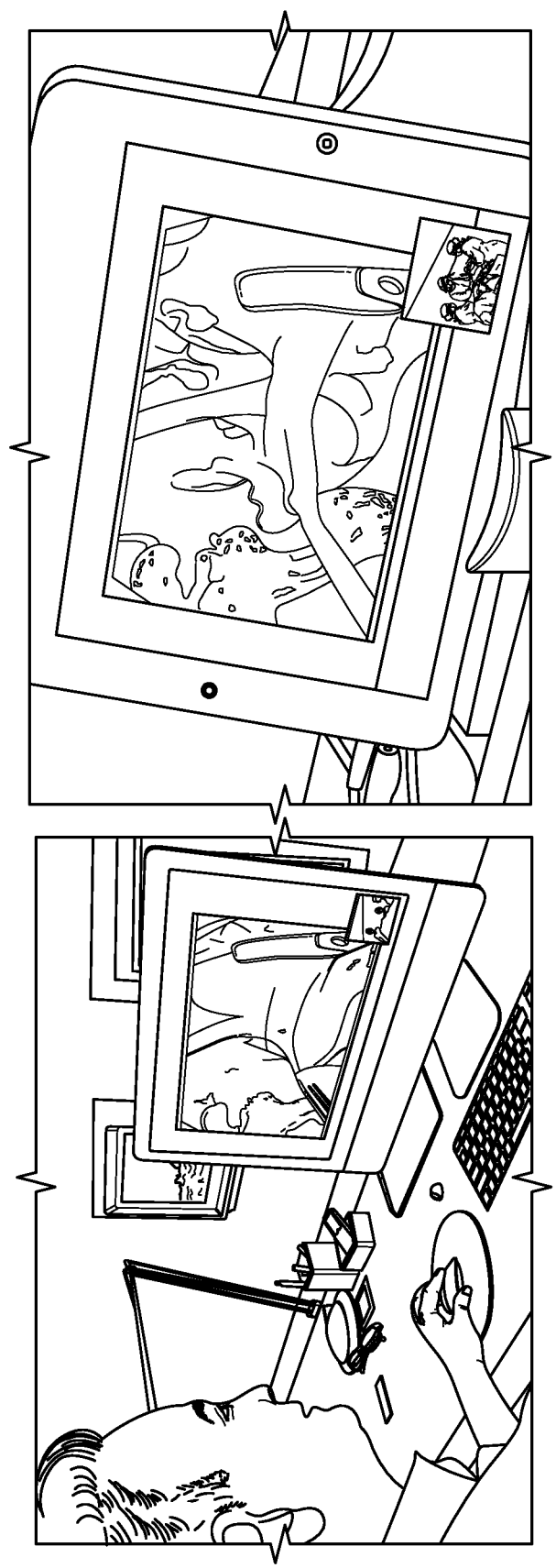
FIG. 11 depicts the preceptor performing graphical indications for the medical team in a real procedure using the system proposed in the present invention.

As can be seen in FIGS. 9-11, the system of the present invention was applied in assisted surgery, where it was used in a real procedure, with the use of the equipment for signal transmission, the object of the present invention, wherein a laparoscopic camera output was connected to the equipment video input (21), 480p analog video, which was routed to the Cerevo LiveShell encoder (12), which performed the adjustment to RTMP standard, sending the signal to a streaming server. The encoder (12) connection was provided via network cable connected to the switch (14) input, which was also responsible for connecting, via network cable, to the router (13), which, in this way, operates in WAN mode.

Router (13) was configured to generate a Wi-Fi network to associate the other elements for the operation of the system. Thus, an iPad® device was used for communication between a surgical team and a remote preceptor. In this case, the preceptor is an authorized physician and having the required knowledge to assist the medical team, where said authorized physician was arranged at an environment completely separate from the place where the surgery was being performed by the medical team; in this example, the preceptor was arranged at a city far away from the medical team.

The preceptor watched the surgery in real time, in addition to interacting with members of the medical team, so as to give opinions on the surgical procedure. The preceptor was provided with a computer, which played the image originating from the medical team, wherein said computer was provided with ScreenMarker® software, which allows graphics interactions over the received image and returned the image with graphics interactions to the iPad® device at the surgery room via Skype® application running on the preceptor computer. Thus, with the iPad® device connected to the Wi-Fi network generated by the router (13), Skype® application and communication with the preceptor were initiated. The application screen sharing tool was launched by the preceptor, so that the image with graphics interactions were transmitted to the surgical team's iPad® device, enabling assistance of the professional. Thereby, it was possible for the preceptor to indicate to the medical team, via video, the locations where the medical operations were to be performed.

The loudspeakers, located on the equipment, are allowed to play the audio with the preceptor's instructions to the medical team.

Example 4—Assisted Examination

The system of the present invention was applied in endoscopy assisted examination, where it was used in a real procedure, with the use of the equipment for signal transmission, the object of the present invention, wherein a endoscopic camera output was connected to the equipment video input (21), 480p analog video, which was routed to the Cerevo LiveShell encoder (12), which performed the adjustment to RTMP standard, sending the signal to a streaming server. The encoder (12) connection was provided via network cable connected to the switch (14) input, which was also responsible for connecting, via network cable, to the router (13), which, in this way, operates in WAN mode.

Router (13) was configured to generate a Wi-Fi network to associate the other elements for the operation of the system. Thus, an iPad® device was used for distance communication between an examiner team and a physician requesting the examination. In this case, the physician requesting the examination assists the medical team and visualizes the examination in real time, so as to monitor the patient situation and predict a subsequent surgery situation.

The requesting physician watched the surgery in real time, in addition to interacting with members of the medical team, so as to give opinions on the procedure and monitor the patient status. The physician was provided with a computer, which played the image originating from the medical team, wherein said computer was provided with ScreenMarker® software, which allows graphics interactions over the received image and returned the image with graphics interactions to the iPad® device at the examination room via Skype® application running on the physician computer. Thus, with the iPad® device connected to the Wi-Fi network generated by the router (13), Skype® application and communication with the requesting physician were initiated. The application screen sharing tool was launched by the preceptor, so that the image with graphics interactions were transmitted to the examiner team's iPad® device, enabling assistance of the professional.

As provided in the system of the present invention, the video broadcast by the examiner team was forwarded to the streaming server, which the requesting physician has access to. The server used is preferably Zoeweb®, which is provided with a tool that allowed the video to be recorded and stored in the cloud, so as to later make this video available such that the physician him/herself may watch the examination again, and to be able to confirm the conclusions on the case, and further, to allow the patient to follow the exam performance, so that the Zoeweb® server makes the recording available thereto.

Further, the Zoeweb® streaming server enables the management of the stored content, so that it was possible to create a video database, enabling access via an URL link shared and accessible by a physician or system administrator, and this URL link is made available to the patient for content access. Furthermore, the server has allowed the video stored in the cloud to be downloaded to a physical server, owned by the medical team or the requesting physician, manually or automatically, i.e., the videos were downloaded manually to the server, and also via an algorithm that performs downloads automatically.

Example 5—Professional Procedure Data Documentation and Database Formation

The feature of the system of the invention comprising sending audio and video signal data to a virtual server provides documentation of all procedures and data for subsequent review, analysis, data abstraction and study/perfecting of the professional procedures performed. This feature provides the formation of a professional procedure database, which also constitutes an object of the invention.

Persons skilled in the art shall consider the knowledge presented herein and may reproduce the invention in the modalities presented and in other variants encompassed by the scope of the appended claims.

What is claimed is:

1. A system for performing and documenting real-time distance assisted professional procedure, comprising:
   a) an equipment (21) for transmitting a signal (S1) from an input signal (SE) emitted by at least one signal source (20), such equipment (21) comprising a video encoder adapted to receive an input signal (SE) and configured to send an output signal (S1), said signal (S1) being a video signal or a video plus audio signal, wherein the equipment (21) comprises at least one encoder (12), at least one router (13), and at least one network switch (14), wherein said at least one encoder (12) and said at least one router (13) are associated with said at least one network switch (14), and wherein said at least one encoder (12), said at least one router (13) and said at least one network switch (14) are integrated in an interior of the equipment (21);
   b) a virtual address (22) receiving the signal (S1) emitted by the equipment (21), directing said signal (S1) to at least one server (23), wherein said at least one encoder (12) is adapted to receive the input signal (SE) and configured to send the output signal (S1) to a virtual address (22); and
   c) such server (23) directing the signal (S1) to at least one communication channel (C1), enabling access to at least one user;
   wherein the user is a spectator (24) or a participant (25),
   wherein when the user is a participant (25), the participant (25) accesses a communication channel (C2) and emits at least one signal (S2), comprising a graphical modification of the signal (S1), to at least one device (26), arranged at a local base, configured to receive said signal (S2), wherein said graphical modification is a graphic editing on the signal (S1),
   wherein the server (23), being a cloud-based platform, is provided with a tool that allows the signal (S1) be recorded and stored in the cloud-based platform, in order to generate a database and to be available for download by controlled access.

2. The system according to claim 1, wherein said communication channel (C2) is of the videoconferencing channel type, screen sharing type, or both, wherein said communication channel (C2) allows access by other users.

3. The system according to claim 1, wherein the communication of said participant (25) with other users is made via modification of the signal (S1), such modification being shared among other users through a screen sharing.

4. The system according to claim 1, wherein the communication channel (C2) is adapted to transmit a command signal to at least one device (26) adapted to receive a command signal, wherein such device (26) performs said command.

5. The system according to claim 1, wherein said video encoder is adapted to adjust the output signal (S1) quality as a function of the quality of the connection detected at the communication channel (C1).

6. The system according to claim 1, wherein said equipment (21) is connected to at least one network router for connection to at least one device (26) comprising one participant (25).

7. The system according to claim 1, further comprising documenting procedures and data at a database for subsequent review, analysis, data abstraction and study/perfecting of the professional procedures performed.

8. A process for performing and documenting real-time distance assisted professional procedure comprising employing a system for performing and documenting real-time distance assisted professional procedure, the system comprising:
   a) an equipment (21) for transmitting a signal (S1) from an input signal (SE) emitted by at least one signal source (20), such equipment (21) comprising video encoder adapted to receive an input signal (SE) and configured to send an output signal (S1), said signal (S1) being a video signal or a video plus audio signal, wherein the equipment (21) is a device for performing and documenting real-time distance assisted professional procedure, the device comprising at least one encoder (12), at least one router (13), and at least one network switch (14), wherein said at least one encoder (12) and said at least one router (13) are associated with the at least one network switch (14), and wherein the at least one encoder (12), the at least one router (13) and the at least one network switch (14) are integrated in an interior of the equipment (21), and;
   b) a virtual address (22) receiving the output signal (S1) emitted by the equipment (21), directing the output signal (S1) to at least one server (23), said server being a cloud-based platform, wherein said at least one encoder (12) is adapted to receive the input signal (SE) and configured to send the output signal (S1) to the virtual address (22); and
   c) said server (23) directing the output signal (S1) to at least one communication channel (C1), enabling access to at least one user,
   wherein said signal source (20) is an image capture device connected to at least one image processor, said image processor sending the input signal (SE) directly to the equipment (21),
   wherein the user is a spectator (24) or a participant (25), and
   wherein when the user is a participant (25), the participant (25) accesses a communication channel (C2), emitting at least one signal (S2) to at least one device (26) configured to receive said signal (S2); and
   the process comprising the steps of:
   receiving, by means of the video encoder (12) comprised in the equipment (21), the input signal (SE) emitted by the at least one signal source (20);
   transmitting the output signal (S1), by the video encoder (12), to the virtual address (22), wherein the video encoder (12) is adapted to adjust the output signal (S1) quality as a function of the quality of an internet connection detected by the video encoder (12);
   directing the output signal (S1) to the server (23) by the virtual address (22);
   directing, by the server (23), the output signal (S1) to the at least one communication channel (C1) enabling access to at least one remote user, wherein the remote user being either a spectator (24) or a participant (25), in which a participant (25) is able to emit the at least one signal (S2), comprising a graphical modification of the output signal (S1), to at least one device (26), arranged at a local base, configured to receive said signal (S2), wherein said graphical modification is a graphic editing on the signal (S1); and
   recording and storing the signal (S1) in the cloud-based platform of the server (23), and generating a database in order to make available the signal (S1) for download by controlled access.

9. The process according to claim 8, wherein the process is an assisted surgery or medical procedure.

10. The process according to claim 8, further comprising employing the equipment (21) as a device for performing and documenting real-time distance assisted professional procedure,
 wherein said communication channel (C2) is of the videoconferencing and screen sharing type, and
 wherein when the user is a participant, the participant (25) modifies the output signal (S1) and sends the signal (S2) to other users and to the at least one device (26) configured to receive said signal (S2) and which is connected to the participant (25).

11. The system according to claim 1, wherein said at least one router (13) is provided with three operational modes, being:
 WAN mode, wherein said at least one router (13) receives an internet signal via network cable and routes it to a Wi-Fi receiver;
 AP mode, wherein said at least one router (13) receives an internet signal via Wi-Fi provided with an external network generated in a local environment; and
 3G/4G mode, wherein said at least one router (13) receives the signal from a 3G/4G modem, and routes an internet signal to other network receivers.

12. The process according to claim 8, wherein said at least one router (13) is provided with three operational modes, being:
 WAN mode, wherein said at least one router (13) receives an internet signal via network cable and routes it to a Wi-Fi receiver;
 AP mode, wherein said at least one router (13) receives an internet signal via Wi-Fi provided with an external network generated in a local environment; and
 3G/4G mode, wherein said at least one router (13) receives the signal from a 3G/4G modem, and routes an internet signal to other network receivers.

13. The system according to claim 6, wherein the connection to the at least one device (26) comprising one participant (25) is a wireless connection.

* * * * *